United States Patent [19]

Mehra

[11] Patent Number: 4,601,738
[45] Date of Patent: Jul. 22, 1986

[54] PROCESS FOR FREEZE PROTECTION AND PURIFICATION OF NATURAL GAS LIQUID PRODUCT STREAMS PRODUCED BY THE MEHRA PROCESS

[75] Inventor: Yuv R. Mehra, Odessa, Tex.

[73] Assignee: El Paso Hydrocarbons Company, Odessa, Tex.

[21] Appl. No.: 758,351

[22] Filed: Jul. 24, 1985

Related U.S. Application Data

[63] Continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ .................................................. F25J 3/02
[52] U.S. Cl. ......................................... 62/17; 55/29; 55/68; 62/20
[58] Field of Search .............. 62/17, 18, 20; 55/68, 55/29, 30, 31, 32; 203/66

[56] References Cited

U.S. PATENT DOCUMENTS

| | | | |
|---|---|---|---|
| 2,238,201 | 4/1941 | Wilson et al. | 196/32 |
| 2,794,334 | 6/1957 | Peaslee et al. | 62/175.5 |
| 2,863,527 | 12/1958 | Herbert et al. | 183/115 |
| 3,690,816 | 9/1972 | Alleman | 423/228 |
| 3,702,296 | 11/1972 | Arnold et al. | 208/341 |
| 3,886,757 | 6/1975 | McClintock et al. | 62/20 |
| 4,233,141 | 11/1980 | Beavon et al. | 208/236 |
| 4,302,220 | 11/1981 | Volkamer et al. | 55/32 |
| 4,305,733 | 12/1981 | Scholz et al. | 48/196 |
| 4,332,596 | 6/1982 | Ranke et al. | 55/18 |
| 4,382,855 | 5/1983 | Ward et al. | 208/236 |
| 4,406,774 | 9/1983 | Cummings et al. | 62/17 |
| 4,430,196 | 2/1984 | Niu | 208/47 |

OTHER PUBLICATIONS

"New NGL Extraction Process", *Gas Processors Report*, Oct. 14, 1985, P.O. Box 33002, Tulsa, Okla. 74153, pp. 7 and 8.

Primary Examiner—Frank Sever
Attorney, Agent, or Firm—Depaoli & O'Brien

[57] ABSTRACT

The Mehra process, for selectively extracting $C_{2+}$ hydrocarbons from a raw natural gas stream to produce a residue gas stream meeting pipeline specifications and a natural gas liquid product, is improved by providing a process for purifying the liquid product. This improved process comprises injecting a stream of methanol into the stream of flashed gases from at least the final flashing stage. The injection preferably occurs prior to condensing the flashed gases and must occur prior to reaching the temperature of hydrate formation. The natural gas liquid product from the demethanizing (stripping) column is then allowed to separate into two phases in a surge vessel. The lower layer of methanol/water/physical solvent is removed, the methanol is recovered for recycling to the flashed gases. The upper layer is decanted as purified natural gas liquid product which meets specifications for gumming compounds if the raw natural gas stream is entirely sweet. If, however, the raw stream is sour or has even small quantities of acidic components, such as $CO_2$, the purified natural gas liquid product is further sweetened with, for example, an aqueous amine treatment.

21 Claims, 7 Drawing Figures

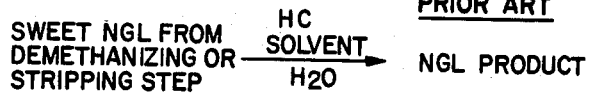
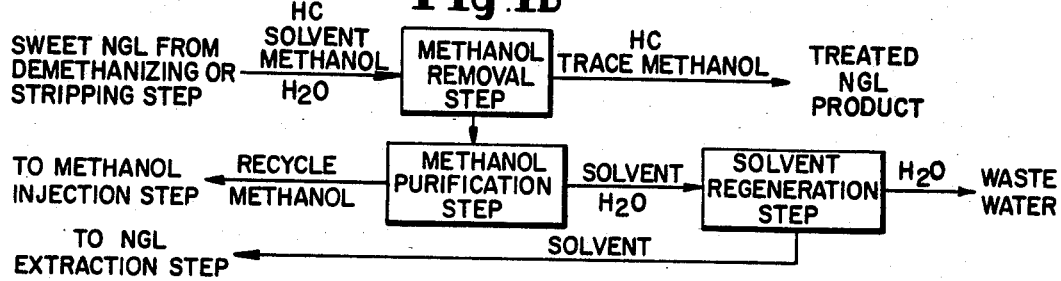
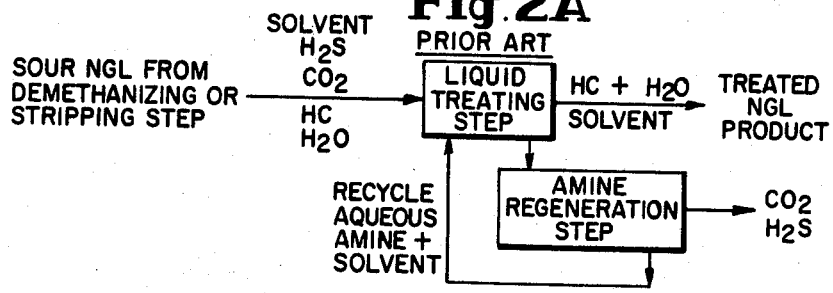
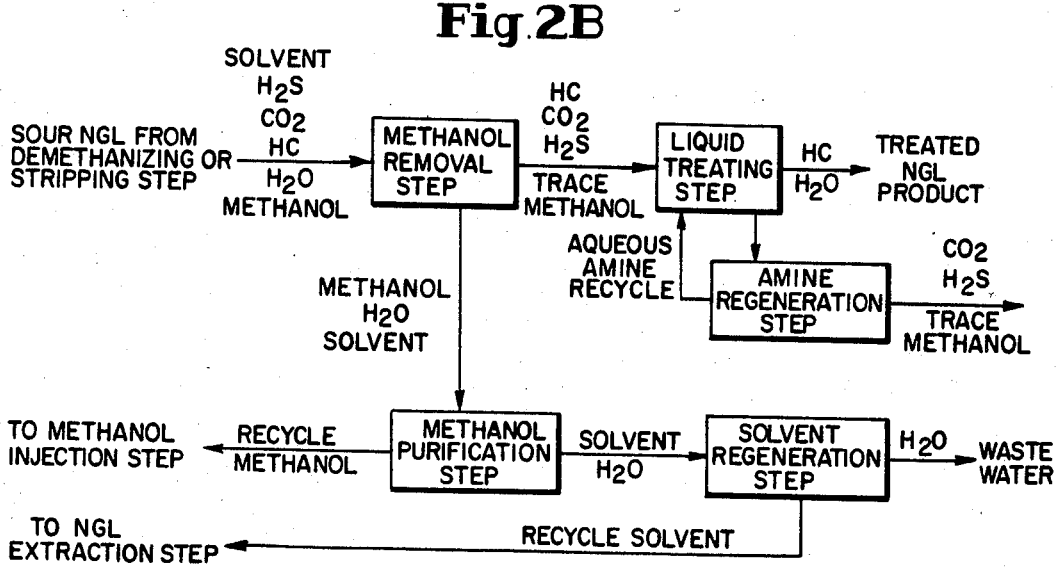

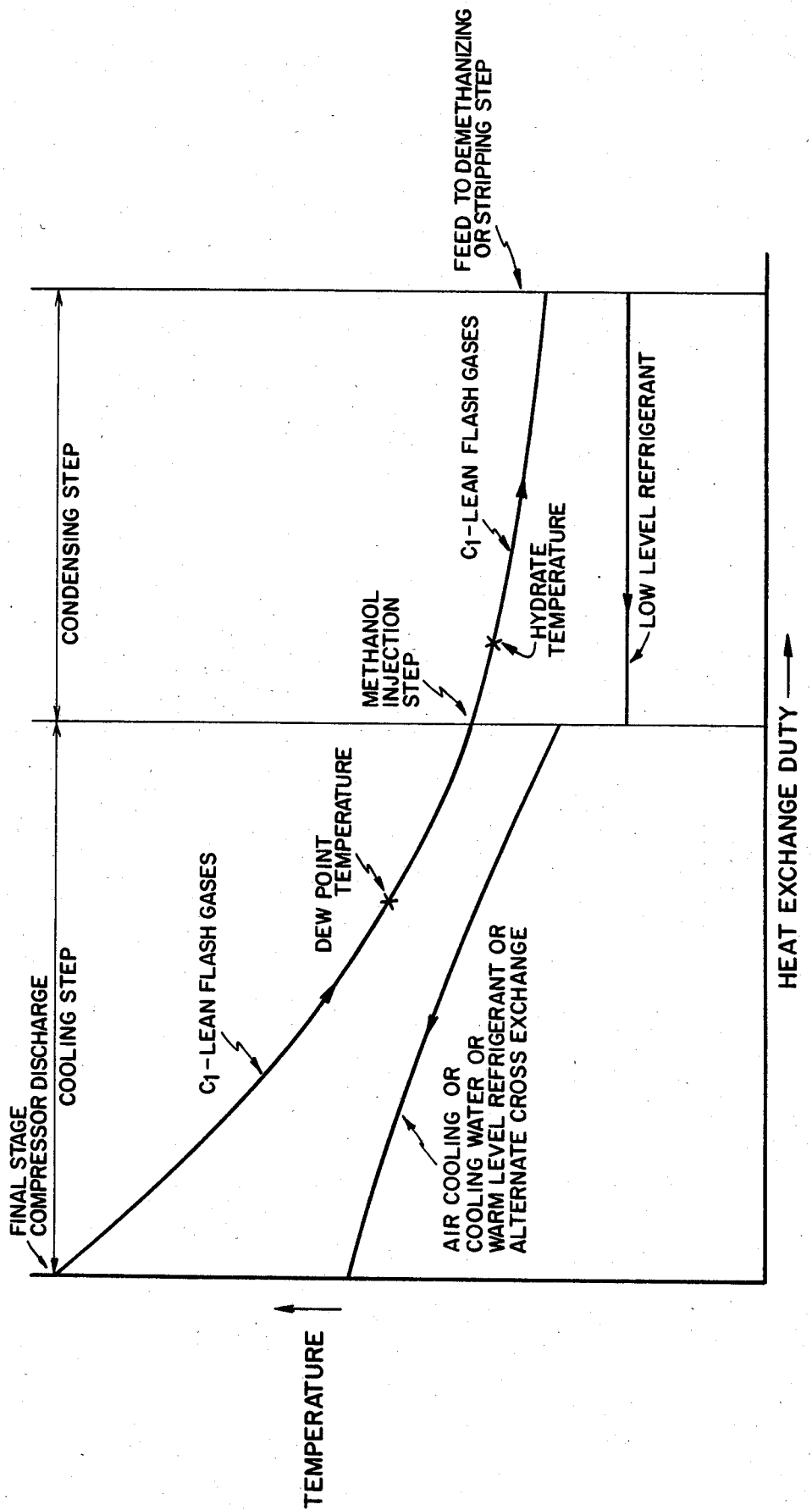

PROCESS FOR FREEZE PROTECTION AND PURIFICATION OF NATURAL GAS LIQUID PRODUCT STREAMS PRODUCED BY THE MEHRA PROCESS

REFERENCE TO RELATED APPLICATIONS

This application is a continuation-in-part of co-pending application Ser. No. 637,210, filed Aug. 3, 1984, of Yuv R. Mehra, entitled "HYDROCARBON SEPARATION WITH A PHYSICAL SOLVENT", now U.S. Pat. No. 4,578,094, which is a continuation-in-part of application Ser. No. 532,005, filed 9-14-83, now U.S. Pat. No. 4,526,594, which is a continuation-in-part of application Ser. No. 507,564, filed 6/24/83, now U.S. Pat. No. 4,511,381, which is a continuation-in-part of Ser. No. 374,270, filed 5/3/82, now U.S. Pat. No. 4,421,535.

BACKGROUND OF THE INVENTION

1. Field of the Invention

This invention relates to flexibly extracting and recovering a stream of $C_2+$ hydrocarbons from a natural gas stream. It more specifically relates to the prevention of hydrate formation during processing of natural gas liquids by the Mehra Process. It further relates to purifying the stream of $C_2+$ hydrocarbons before use thereof as a natural gas liquid product stream.

2. Review of the Prior Art

Natural gas is a mixture of hydrocarbons, including methane, ethane, propane, and various amounts of higher molecular weight hydrocarbons together with acid gases, such as $CO_2$ and/or $H_2S$. A "dry" gas is one containing predominantly methane with some ethane, propane, and butane with a very low hydrocarbon dew point. The heavier the hydrocarbons, such as pentane and higher homologs that are present in the gas, the higher the hydrocarbon dew point. For pipeline transmission, enough of the heavier hydrocarbons must be removed to lower the dew point without losing BTUs to meet specifications. In the past, gas with large quantities of high molecular weight hydrocarbons have been passed through gasoline extraction plants and/or dew point control stations to lower the dew point. Also, frequently the gas has required conditioning to remove sulfur compounds and carbon dioxide.

A natural gas stream coming from the wellhead is also usually saturated with water at its ambient temperature which may have a range of 75°–120° F. so that its water content may vary from 20 pounds to more than 50 pounds per million standard cubic feet. However, difficulties are frequently met while pumping such natural gas, such as formation of ice and hydrates or the accumulation of water which can block the flow as well as cause corrosion, unless the water content is reduced to a value of less than 12 pounds, preferably less than 7 pounds, of water per million standard cubic feet of natural gas. In terms of dew point, a natural gas having a dew point of 30° F., preferably 20° F. or lower, is generally considered safe for transportation in a pipeline. Dehydration can be carried out under a wide range of pressures from 15 to 5,000 PSIG, but it is usually carried out at pipeline pressures of 500–1,500 psig.

Dehydration and sweetening of natural gas has been done with physical solvents, as taught in U.S. Pat. Nos. 3,362,133, 3,770,622, and 3,837,143, but always with an economic penalty from losses of hydrocarbons that were absorbed with the acid gases. Such losses can be appreciated in view of the relative solubilities of the acid gases and the hydrocarbons in physical solvents.

The Mehra process took advantage of the liabilities of the prior art processes by utilizing the relative solubilities of the hydrocarbons in physical solvents for the specific purpose of isolating and recovering the hydrocarbons. Specifically, the Mehra process handles any natural gas, from very sour to entirely sweet, in the same equipment while simultaneously dehydrating the gas and recovering the heavier hydrocarbons with a physical solvent, as disclosed in U.S. Pat. Nos. 4,421,535 and 4,511,381 of Yuv R. Mehra, both of which are herein incorporated by reference. The compositions of its liquid hydrocarbon product and of its residue natural gas product can be readily adjusted in accordance with market conditions so that profitability of the extraction operation can be maximized at all times and on short notice. This process thereby produces a liquid hydrocarbon product having a composition which is selectively versatile rather than fixed, as in prior art processes.

The inlet natural gas streams which may be treated with a physical solvent according to the Mehra process include the following:

A. natural gas saturated with water;
B. natural gas at less than saturation with water;
C. sour natural gas;
D. sour natural gas which is pre-sweetened in gas phase with an aqueous amine solution;
E. sweet natural gas; and
F. dry natural gas.

Such versatility is achieved by flexibility in certain operating conditions and by use of certain additional steps that are not used in the prior art. These conditions and steps are listed as follows, in order of importance:

(1) varying the flow rate of a physical solvent with respect to flow rate of the natural gas stream in an extraction column to produce the rich solvent;

(2) varying the flashing pressure for one or more of the successive flashing stages for the rich solvent;

(3) recycling the flashed $C_1+$ undesirable gases from the first flashing stage and, selectively, also the second flashing stage to the extraction column;

(4) compressing, cooling, and condensing the flashed gases from the remaining flashing stages to form a crude liquid;

(5) rejecting and returning to the residue gas line selected components of the crude liquid, viz., methane (demethanizing), methane plus ethane (de-ethanizing), methane, ethane, and propane (depropanizing), or methane, ethane, propane, and butanes (debutanizing) in a stripping column for the crude liquid by:
   (a) varying the pressure in the column, and
   (b) varying the temperature at the bottom of the column; and (6) recovering the remaining components as the natural gas liquid product.

However, daily changes in market conditions may also cause the price of a single liquid hydrocarbon heavier than ethane to drop below its fuel price so that this hydrocarbon should be selectively rejected, but there was no way in the prior art or in these two patents of doing so without also rejecting all components of lower molecular weight. For example, if the price of ethane was below its fuel value, it could be rejected with methane, as taught in U.S. Pat. Nos. 4,421,535 and 4,511,381, but if the price of propane was below its fuel value while the price of ethane was above its fuel value, both of these hydrocarbons would have to be rejected together because no method existed for separating them. Accordingly, U.S. Pat. No. 4,526,594 of Yuv R. Mehra, which is also incorporated herein by reference, provides a process that is useful when changes in the market prices for individual hydrocarbons in liquid form cause the market price for an individual hydrocarbon liquid to fall below its fuel price. Such prices change on a daily basis so that it becomes advantageous to be able to extract all of the $C_2$–$C_5+$ hydrocarbon liquids while rejecting and returning to the residue gas line one or more of the $C_2$–$C_4$ hydrocarbons that are priced below their fuel values. The extraction plant can thereby be operated at optimum profit levels at all times.

The process of U.S. Pat. No. 4,526,594 accomplishes this selective rejection by subjecting the rejected components of the crude liquid to a second extraction with a portion of the same physical solvent to produce a gas stream of $C_1$ or $C_1+C_2$, which is returned to the residue gas line, and a second rich solvent stream which is singly flashed to produce an overhead gas stream and a liquid mixture which is regenerated to produce the physical solvent stream for the extracting. This gas stream is compressed, cooled, and condensed to form a second crude liquid stream. This liquid stream is split. The bottom portion, of $C_3$'s or $C_3+C_4$'s or $C_4$'s only, is sent to the residue gas line, and the top portion, of $C_2$ or $C_2+C_3$ or $C_3$, is combined with the liquid product from the stripping column.

The absorption principle leads to an alpha or relative volatility for methane with respect to ethane of slightly less than 5 for almost all known absorption liquids. However, the relative volatility for methane with respect to ethane in the presence of dimethyl ether of polyethylene glycol (DMPEG) is 6.4, indicating that it is more selective toward ethane than other absorption liquids. N-methyl pyrrolidone (NMP) and dimethyl formamide (DMF) have relative volatilities for methane/ethane of 5.3 and 8.5, respectively. However, the solubility of hydrocarbons in NMP is 0.03 standard cubic feet per gallon (SCF/gal) and in DMF is 0.04 SCF/gal; these are low when compared to 1.0 SCF/gal for DMPEG.

Therefore, it is the combination of improved selectivity towards ethane and the hydrocarbon loading capacity of dimethyl ether of polyethylene glycol that makes it a superior absorption solvent for separating and recovering the components of a natural gas stream that are heavier than methane, in accordance with the disclosures of the Mehra process in U.S. Pat. Nos. 4,421,535, 4,511,381, 4,526,594, and U.S. application Ser. No. 637,210. The minimum qualifications for a physical solvent are a minimum relative volatility of methane over ethane of 5.0 (thereby defining its improved selectivity toward ethane over methane) and minimum solubility of 0.25 standard cubic feet per gallon of the solvent (thereby defining its hydrocarbon loading capacity). However, the ideal physical solvent would have a selectivity toward ethane over methane as high as 10.0, and simultaneously would possess a hydrocarbon loading capacity of about 3.0 SCF/gal. This combination also enables solvent flow rate variation and flashing-pressure variations to be particularly useful for flexibly producing liquid products having selected hydrocarbon compositions.

This physical solvent is selected from the group consisting of dialkyl ethers of polyalkylene glycol, N-methyl pyrrolidone, dimethyl formamide, propylene carbonate, sulfolane, and glycol triacetate. The solvent is preferably selected from the group consisting of dimethyl ether of polyethylene glycol, dimethyl ether of polypropylene glycol, dimethyl ether of tetramethylene glycol, and mixtures thereof, and the solvent most preferably is dimethyl ether of polyethylene glycol containing 3–10 ethylene units and having a molecular weight of 146 to 476.

The glycol can be branched, such as polypropylene glycol. The basic difference between the behaviors of ethyl and propyl groups is the affinity for water for the ethyl and greater affinity for hydrocarbons for the propyl group. A mixture of dimethyl ethers of polyethylene and polypropylene glycol in various combinations is consequently suitable for recovering ethane plus heavier hydrocarbons from a natural gas. In such a mixture, the content of dialkyl ether of polyethylene glycol should be a minimum of 20% by volume, with dialkyl ether of polypropylene glycol being limited to 80% by volume maximum.

$CO_2$ and $H_2S$ have solubilities in DMPEG that are very close to the solubilities of propane and pentane in this solvent. Therefore, it is difficult to separate these acidic materials from the desirable gases when treating sour natural gas. The prior art has tended to perform this separation before removing hydrocarbons, thereby requiring large-capacity equipment and losing significant quantities of desirable hydrocarbons with $CO_2$ and $H_2S$ vent streams. Widespread usage of DMPEG has obviously been avoided.

In one of the embodiments of the Mehra process, $CO_2$ and $H_2S$ are allowed to remain with the desirable gases until final stages in the process where they are removed as liquids, thereby requiring smaller and less expensive equipment because the equipment's size is determined by mode of treating, i.e., in gas phase or liquid phase.

This treatment procedure requires the usage of substantially larger quantities of DMPEG than has been recommended by the prior art, since the quantity of $C_2+$ hydrocarbons is generally larger than the quantities of $CO_2$ and $H_2S$ in a relatively sweet natural gas stream. There is, consequently, enough absorption capacity in the DMPEG stream when equilibrium is reached that the acidic materials in the recycle stream and in the sour natural gas can be completely removed, thereby producing a sweet methane-rich stream from the top of the extractor that meets pipeline specifications.

An advantage of this treatment method over those of the prior art is that a single plant can accept a very wide variety of natural gas streams, from very acidic to completely sweet, simply by utilizing the acid removal unit (e.g., an amines process) to a selective extent or even by by-passing it entirely. Although liquid-phase sweetening requires a lower capital investment and has lower operating costs than gas-phase sweetening, there are compensating factors in favor of gas-phase sweetening. These include the use and pumping of smaller quantities of solvent and the availability of maximum flexibility as to hydrocarbon composition in the liquid product.

It is preferred that amine processes (MEA, DEA, or DGA) be utilized for removing acid gas components ($CO_2$ and $H_2S$) in gas phase before proceeding with this invention process. The sweet natural gas thus produced will be saturated with water vapor at the pipeline pressures and operating temperatures because any amine process is aqueous based and introduces water vapor into the natural gas stream.

Alternatively, acid gas components can be removed in the liquid phase downstream of processing according to this invention process by amine processes using MEA or DEA. For maximum flexibility of recovering ethane versus rejecting ethane while recovering all of propane plus heavier hydrocarbons in contrast to recovering propane versus rejecting ethane and propane while recovering all of butane plus heavier hydrocarbons, it is preferred that the sour natural gas stream be treated with aqueous amine processes in gas-phase operation in order to extract $CO_2$ and $H_2S$ components without losing any hydrocarbons.

As disclosed in a paper entitled "High $CO_2$-High $H_2S$ Removal With SELEXOL Solvent", that was presented by John W. Sweny at the 50th Annual Gas Processors Association Convention, Mar. 17–19, 1980, the relative solubility of $CO_2$ over methane in a mixture of dimethyl ethers of polyethylene glycol (DMPEG) is 15.0 and the relative solubilities of various hydrocarbons present in a natural gas stream are disclosed as varying from 6.4 to about 165, whereas the similar relative solubility of water is 11,000.

These data appear to indicate that when a physical solvent, such as DMPEG, is flashed to lower pressures, the hydrocarbons separated from the natural gas stream should be essentially dry with respect to water because they have much less relative solubility in the solvent when compared to the solubility of water. However, in the Mehra process, these hydrocarbons are compressed, cooled, and condensed before they are fractionated to make a desired natural gas liquid product (NGL). In consequence, when the condensing temperature of the compressed gases is lower than their hydrate temperature, any water that may be present in these condensed hydrocarbons will tend to freeze in the equipment and thereby prevent the Mehra process from continuing to operate.

It is therefore pertinent that a recent discovery has been made that water, as determined by equilibrium conditions, will nevertheless be present with the flashed hydrocarbon gases, especially when the solvent separation from hydrocarbons is carried out at near-atmospheric pressures, regardless of the multifold differences between the solubility of water and the solubility of heavier components of the natural gas stream in the physical solvent. The presence of water also results in poor measurement of natural gas liquids and causes errors, thereby resulting in loss of revenues. There is consequently clearly a need for a method for removing such residual water from the NGL product.

It has also been recently discovered that, especially when vacuum or heated flashes are utilized in the Mehra process, there is a tendency for some of the solvent to remain with the flashed hydrocarbon gases. When these gases are compressed, cooled, and condensed, a major portion of this flashed-over solvent can be recovered in interstages, but a residual amount will continue to stay with the NGL product. This residual amount of solvent will essentially end up in a natural gasoline fraction ($C_5+$) of the NGL product and will eventually act as a gumming compound which is undesirable for the gasoline when it is used for motor fuel. Thus there is also a need for a method of removing this residual solvent from the natural gas liquid product.

It is known in the prior art that the problem of freeze can be avoided by drying the gases, before the condensation step and after compression thereof, with: (a) activated alumina, (b) molecular sieves, (c) glycol injection, or (d) methanol injection. Methods of dehydrating gas streams and products therefrom in the prior art with methanol appear to concentrate on cold temperature treatments when liquid desiccants or solvents are used. Other methods include sequential treatments with two or more solvents, the desiccant solvent being used on the gas stream generally after sulfur-absorbing treatment.

U.S. Pat. 2,238,201 describes a process of purifying hydrocarbon liquids, especially mixtures of hydrocarbons such as gasoline or lower boiling hydrocarbons, with a primary, secondary, or tertiary aliphatic amine, or mixtures thereof. The amine absorbent is a water-soluble, basic-reacting amine having a boiling point above that of water and a high distribution ratio for water over hydrocarbons. Satisfactory amines are members of the ethanolamines, isopropanolamines, polyethylenes and polypropylenes, the aminopropanediols, and the diaminopropanols. Preferred compounds are monoethanolamine, diaminoisopropanol, and particularly diethylene triamine and triethylene tetramine, or commercial mixtures thereof. The liquid hydrocarbon is admixed with an aqueous amine solution and then passed into a large gravity separator from which the hydrocarbon liquid containing some dissolved amine is drawn into a second mixing system wherein it is thoroughly mixed with pure water and passed through a second gravity separator. A purified hydrocarbon liquid is withdrawn from the top layer of the second gravity separator. The lower layers of both gravity separators are drawn off, combined, and heated to expel volatile impurities and regenerate the amine solution.

In U.S. Pat. No. 2,794,334, a method is taught which comprises countercurrently contacting a hydrocarbon gas with a refrigerated aqueous solution of 60–90% methyl alcohol in a specific manner and in sufficient volume to liquefy the liquid fraction as the refrigerant flows downwardly in a column countercurrently to the unliquefied hydrocarbon gas flowing upwardly.

U.S. Pat. No. 2,863,527 relates to the purification of combustible gases containing at least one of carbon monoxide, hydrogen, and methane, such as those gases obtained from distilling or gasifying solid carbonaceous fuels. The purification includes washing the gas at temperatures below zero and as low as −30° C., while at a pressure of at least two atmospheres, with a polar organic washing agent (methanol being preferred) having a freezing point below the washing temperature and being substantially chemically inert to the impurities to be removed. Removal of non-polar constituents from the gas is partially accomplished by the methanol but is aided by the addition of a non-polar washing agent such as low-boiling aliphatic or cyclic straight-chained or branched-chained hydrocarbons. It is preferred to use eutectic mixtures, with a low solidification point, which contain about 1–50% water as the polar organic washing agent in order that they can absorb water from the gas.

U.S. Pat. No. 3,690,816 relates to removing impurities, such as hydrogen sulfide, carbon dioxide, and/or water, from a hydrocarbon gas or liquid. The gas to be purified is passed into an absorber in which it is countercurrently contacted by cool, lean, aqueous monoethanolamine. Purified gas leaves the top of the absorber.

Rich absorbent solution leaves the bottom of the absorber, passes through a heat exchanger in which it is heated, and then enters a stripper column, within which stripping vapors from heated stripper bottoms rise to an overhead condenser and reflux drum. The impurities are removed from the reflux drum while reflux is returned to the top of the stripper. Hot, lean, aqueous monoethanolamine solution is removed from the bottom of the stripper and passed through the same heat exchanger for cooling and recycling to the top of the absorber.

U.S. Pat. No. 3,886,757 describes a process for treating a stream of natural gas to reduce the moisture content thereof by washing the gas with a liquid desiccant-antifreeze agent, such as aqueous methyl alcohol containing about 15-40 wt. % water. The treated gas stream is then cooled to a low temperature, such as $-100°$ F., so that all methanol and gasoline therein are substantially condensed. These cold liquids are then removed in a separator and scrubbed with water to remove alcohol from the hydrocarbon liquids. The bottoms from the first contactor and from the separator are fractionated to recover the methyl alcohol.

U.S. Pat. 4,233,141 is directed to purifying liquid hydrocarbon gases (LPG) of $H_2S$, COS, and, if also present, $CO_2$ by contacting the LPG with an aqueous solution of diethanolamine at a temperature below the hydrolysis temperature for COS in order to remove the bulk of the $H_2S$ and $CO_2$. The LPG is then heated to hydrolysis temperature and mixed with hot diethanolamine solution so that the COS is hydrolyzed to $H_2S$ and $CO_2$. The LPG (under sufficient pressure so that it is still liquid and still contains the products of hydrolysis) is then separated from the hot amine solution, cooled, and again brought into contact with diethanolamine solution so that all $H_2S$ and $CO_2$ are extracted therefrom.

U.S. Pat. No. 4,302,220 describes a process for simultaneously removing water and hydrogen sulfide from gases by absorbing both materials under superatmospheric pressure with polyethylene glycol dialkyl ethers, stripping the hydrogen sulfide from the loaded solvent, removing the water taken up thereby, and recycling the regenerated solvent for contact with the loaded gases. The solvent contains 0.01-20% by weight, based on a solvent mixture, of an alcohol or ether boiling in the range of from 50° to 140° C. The alcohols used are preferably aliphatic alcohols having 1-5 carbon atoms, methanol being preferred.

U.S. Pat. No. 4,305,733 furnishes a method for the recovery of a methane-rich natural gas from a sour natural gas by initially chilling the natural gas so that water, heavy hydrocarbons, lighter hydrocarbons, and acid gases are condensed for further processing. The gas is then scrubbed with dimethyl isopropyl ether of ethylene glycol at a temperature of $-10°$ C. to remove hydrogen sulfide. The scrubbed gas is then contacted with liquid methanol at $-50°$ C. to remove carbon dioxide. The charged methanol is expanded in a liquid turbine to produce a liquid phase of generally methanol-containing solubilized $CO_2$ and a gaseous phase consisting of hydrocarbons solubilized in or entrained by the methanol. The expanded methanol is regenerated, and dissolved $CO_2$ is removed. The gas, after scrubbing with methanol, is essentially pure methane.

U.S. Pat. No. 4,332,596 teaches the selected removal of sulfur compounds, such as $H_2S$ and carbonyl sulfide (COS), from moist gaseous mixtures by scrubbing these mixtures at a temperature below 0° C. with toluene or xylene as the scrubbing liquid, after the moist gaseous mixture has been contacted with liquid methanol before cooling the mixture to scrubbing temperature. The liquid methanol is partially vaporized so that a methanol concentration of above 2%, preferably 3-8% to about 30% by weight, is maintained in the scrubbing liquid to be recycled from the sump of the thermal regenerating column to the scrubbing column.

U.S. Pat. No. 4,382,855 discloses a process for removing hydroxy-substituted and/or mercapto-substituted hydrocarbons from coal liquids by contacting the liquids with an aqueous composition containing an alkanolamine, thereby providing a two-phase mixture, and then separating the mixture into an aqueous extract phase and a naptha-rich raffinate phase.

U.S. Pat. No. 4,430,196 teaches the neutralization of acidic components in petroleum refining units by adding dimethylaminoethanol and/or dimethylisopropanolamine as a neutralizing agent. When sour crude is to be refined, it is desirable that dimethylisopropanolamine be used in conjunction with dimethylaminoethanol. The neutralizing agents are added in an amount sufficient to elevate the pH of the condensate, as measured at the accumulator, to 4.5-7. Use of a neutralizing agent minimizes corrosive attack on the metals normally used in the low temperature sections of a refinery process system, where water is present below its dew point.

When the intended use of a natural gas is not hampered by the presence of $CO_2$, the raw natural gas may not be treated with an aqueous amine solution. Similarly, if both $CO_2$ and $H_2S$ are present in the raw natural gas, the treatment or "wash" with the aqueous amine solution may be sufficient only to remove the $H_2S$. Such "rough and fine washes" are described in U.S. Pat. No. 4,382,855.

The relatively sweet inlet natural gas from a rough amine wash to the Mehra process may contain small amounts of acid gases, particularly $CO_2$, which the physical solvent will remove from the natural gas. When the rich solvent is flashed, the $CO_2$ leaves with the $C_3$-flashed gases and remains in the liquid natural gas products.

There is accordingly a need for a process for sweetening the NGL product of the Mehra process by removing small quantities or even traces of acid components when sour natural gas has been given merely a rough wash selectively to remove $H_2S$ to prepare the inlet natural gas for the Mehra process.

SUMMARY OF THE INVENTION

It is accordingly an object of this invention to provide a process for preventing freeze up of equipment because of the presence of water prior to the condensing step of the Mehra process.

It is also an object to provide a process for removing small quantities of solvent from recovered natural gas liquid products of the Mehra process.

It is additionally an object to provide a process for removing water from the recovered natural gas liquids of the Mehra process in order to minimize volume and gravity measurement difficulties created by water content in the NGL products at up to the saturation level.

It is further an object to provide a process for removing trace quantities of acidic components from the NGL products of the Mehra process.

For this invention, activated alumina beds are not preferred for dehydrating the $C_1$-lean flashed gases, even though they are capable of dehydrating gases to a required dew point, because such beds require significant pressure drops and capital investment requirements. Also for this invention, molecular sieves are not preferred because (1) the dew point temperature is not extremely low and is of the order of $-30°$ F., (2) they cause a significant pressure drop which makes them energy intensive, and (3) they require significant capital investment because of their intermittent operation and regeneration requirements. Further, in this invention, glycol injection is not preferred, even though the temperature requirement can be met, because the commercially available glycols have a tendency to cause hydrocarbon losses. For this invention, however, methanol injection is preferred because methanol is light in weight, has a gravity equivalent to that of water which thereby allows it to be separated from the natural gas liquid products, is totally miscible with water, is easily separable from water by simple fractionation, and will not absorb hydrocarbons from recovered NGLs that could result in losses thereof and would be detrimental to the objectives of the Mehra process.

In accordance with these objects and the principles of this invention, this process comprises injecting methanol into the flashed gases after compressing and cooling, but before condensing and prior to being fed to the demethanizing or stripping column, thereby producing a methanol/water/solvent solution that is a part of the NGL recovered as bottoms in the demethanizing or stripping column. The process further comprises receiving the bottoms in a surge vessel and therein separating the solution of methanol, $H_2O$, and solvent from the NGL by gravity differences and then feeding the separated solution to a methanol-distillation column and therein separating the traces of water and solvent from the methanol which is recycled to the $C_1$-lean flashed gases for re-injection.

Summarizing the invention as an improvement in a continuous process for producing: a liquid hydrocarbon product having a selected composition, that is selectively adjustable to substantially any selected degree in accordance with market conditions, and a residue natural gas stream of pipeline quality, that selectively includes ethane ($C_2$), propane ($C_3$), and butane ($C_4$) by extraction of an inlet natural gas stream, with a stream of a physical solvent to produce a rich solvent stream in addition to the residue natural gas stream, the rich solvent stream being flashed to at least as low as 2 psia to produce: (a) a stream of $C_1$-rich flashed gases which are recycled to extraction with the physical solvent stream, (b) a stream of $C_1$-lean flashed gases which are compressed, cooled, and condensed for demethanizing to produce a selected stream of $C_1$–$C_4$ rejected gases and a natural gas liquid product, and (c) a recycle solvent stream that is split into a major solvent stream and a solvent slipstream which is regenerated to form a lean-and-dry solvent stream for recycling to the extraction, this improvement comprises preventing the formation of hydrates within the $C_1$-lean flashed gases and removing water and residual solvent from the natural gas liquid product to form a purified natural gas liquid product. Specifically, the improved process comprises the following steps:

A. adding methanol to the stream of $C_1$-lean natural gases, prior to achieving the temperature for hydrate formation;

B. after the demethanizing, separating the mixture of a methanol/water/solvent solution and a natural gas liquid product into two phases, the lower phase being the solution of methanol, water, and solvent;

C. removing the lower phase and fractionating the solution to recover the methanol overhead and a stream of water and solvent which is either removed as waste water or recycled to the solvent regeneration step in order to recover solvent; and D. recycling the recovered methanol to the $C_1$-lean flashed gas stream in Step A for freeze protection.

In this improved process, the methanol is preferably injected into the stream of $C_1$-lean flashed gases after compressing and cooling but before reaching the hydrate formation temperature during condensing thereof. The condensed stream of $C_1$-lean flashed gases/methanol/water/solvent solution is at a temperature of not less than $-30°$ F., not more than $+60°$ F., and at a preferred maximum pressure of 500 PSIA. Preferably the solvent solution is at a temperature of $+30°$ F. to $-20°$ F.

The purified natural gas liquid product is recovered as the upper phase of the two phases. It is substantially free of both water and residual solvent but may contain traces of methanol.

If sour components such as $CO_2$ and $H_2S$ are present in the inlet gas and residual amounts or even traces thereof remain in the NGL product, these components are removed from the NGL product by treating, e.g., with an aqueous amine solution. It is preferred that the methanol/$H_2O$/solvent solution according to this invention be removed from the NGL product prior to treatment with the aqueous amine solution.

BRIEF DESCRIPTION OF THE DRAWINGS

FIGS. 1A and 1B illustrates the improvement to the Mehra process that is represented by the invention over prior related United States patents and applications and when processing a sweet natural gas.

FIGS. 2A and 2B illustrates the improvement to the Mehra process that is represented by the invention over prior related United States patents and applications and when processing a sour natural gas.

FIG. 3 defines the relationship of the methanol injection to the hydrate formation temperature of the $C_1$-lean flashed gases.

DETAILED DISCUSSION OF THE INVENTION

Figure 4:
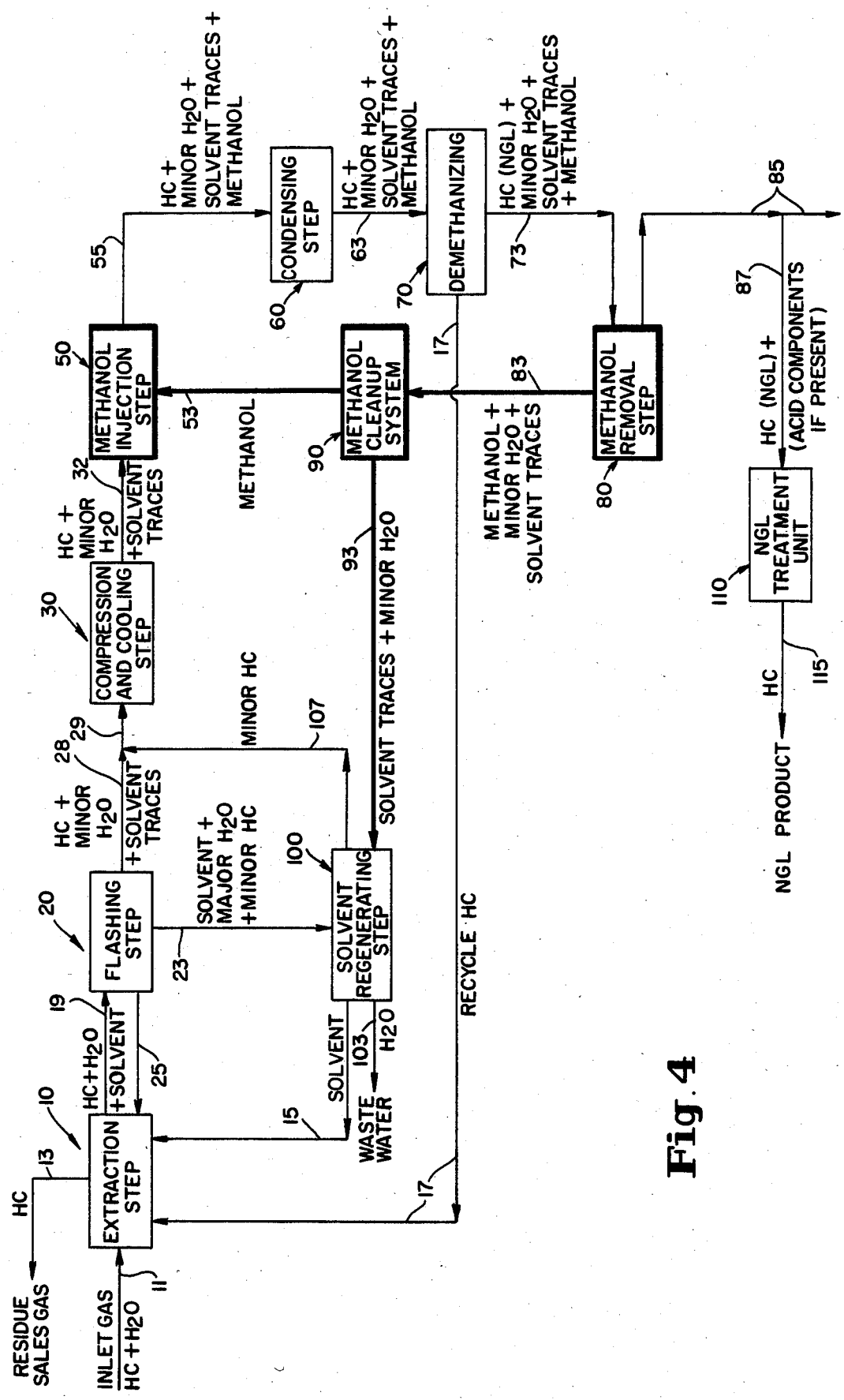
FIG. 4 is a schematic representation of an improved Mehra process having a system for freeze protection and a system for NGL product treatment.

In FIG. 1A of the drawings, sweet NGL from the demethanizing or stripping step is shown as containing hydrocarbons, solvent, and water to form the NGL product, according to the three Mehra patents and one Mehra patent application as prior art. FIG. 1B illustrates the present invention for sweet NGL, with block diagrams to show the steps of methanol removal, methanol purification, and solvent regeneration to produce treated NGL product containing only hydrocarbons and a trace of methanol.

In FIG. 2A of the drawings, sour NGL from the demethanizing or stripping step is shown as being treated with aqueous amines to produce a treated NGL product containing hydrocarbons, water, and solvent, according to the same three Mehra patents and one application as prior art. FIG. 2B illustrates the invention for sour NGL with block diagrams to show the steps of methanol removal, liquid treating with aqueous amines, amines regeneration, methanol purification, and solvent regeneration to produce treated NGL product containing only hydrocarbons and water.

The present invention is applicable to any of the Mehra processes. It is shown in the drawings, as described hereinafter, in combination with the processes of U.S. Pat. Nos. 4,421,535 and 4,511,381. It is equally applicable to the improved Mehra process disclosed in U.S. Pat. No. 4,526,594 and particularly to the improved Mehra process described in Ser. No. 637,210, now U.S. Pat. No. 4,578,094, wherein a slipstream of stripped solvent from the atmospheric flashing stage or from the vacuum flashing stage is regenerated and passed, as lean solvent, to a second extraction stage for removing traces of water from the gas leaving the first extraction stage and for producing a residue gas stream having the required maximum content of water per million standard cubic feet. The remainder of the solvent from the atmospheric flashing stage, or from the vacuum flashing stage, is recycled, as the main solvent stream containing no more than 15 mol. % $C_5+$, to the first extraction stage for countercurrent extraction of the inlet natural gas stream which is saturated with water and contains desirable hydrocarbons. In this situation, the main solvent stream tends to be more heavily laden with water than in the basic Mehra process because the second extraction stage can be relied upon for completely removing all necessary traces of water from the natural gas. It has been discovered, however, that the flashed gases from the atmospheric and vacuum flashing stages tend to have more water than suggested in the basic Mehra process.

For any Mehra process scheme, the $C_1$-lean flashed gases from the atmospheric flashing stage and, if present, additionally from the vacuum flashing stage must not contain more water than is permitted by the hydrate temperatures. The present invention is intended to provide means for preventing hydrate formation by injection of methanol into the $C_1$-lean flashed gases, preferably after compression and cooling but before condensing occurs. It is satisfactory, however, to inject the methanol during the cooling operation. This requirement is further illustrated in FIG. 3.

FIG. 3 specifically teaches that the $C_1$-lean flash gases are at maximum temperature after compression and are lowered in temperature by heat exchange with air, water, warm level refrigerant, or another process stream in alternate cross exchange as sensible heat is removed. The dew point temperature is reached and passed as condensation begins. Then methanol injection occurs, between the heat exchange step and the condensing step, which utilizes a low level refrigerant, wherein latent heat is removed and the hydrate temperature (without methanol injection) is reached and passed.

In the demethanizing unit, the methane is selectively and almost entirely removed from the remainder of the flashed gases, but the methane may be selectively combined with all or a portion of the ethane or with all or a portion of the ethane and the propane, if desired, in order to meet economic criteria and as set forth in U.S. Pat. Nos. 4,421,535; 4,511,381; 4,526,594; and U.S. application Ser. No. 637,210 now U.S. Pat. No. 4,578,094. The remainder of the hydrocarbon gases, the methanol, the water, and any residual solvent are isolated as bottoms in the demethanizing column. The demethanizer bottoms, consisting primarily of methanol/NGL mixture, is sent to an NGL surge vessel in which the methanol/water/solvent solution is isolated as a lower layer by allowing adequate residence time to settle due to the gravity differences between methanol/$H_2O$/solvent and NGL. The lower layer is withdrawn and sent to the methanol purification column in which water and solvent are isolated at the bottom of the column as waste and methanol from overhead is recycled to the $C_1$-lean flashed gases for re-injection.

Depending upon the economics and operating conditions and quantity of solvent present in the bottom stream, the mixture of $H_2O$/solvent may be recycled to the solvent regeneration column, whether on a full stream or on a slipstream service, in order to recover the expensive solvent and thereby enable the modified Mehra process to produce only one waste water stream.

The process of this invention functions as insurance to prevent hydrate formation within the equipment of the Mehra processes, to keep the natural gas liquid product within specification for water content in order to improve the NGL measurement, and to remove solvent from the NGL product which may act as a gumming material when the natural gas liquid product is utilized as gasoline.

Because of the characteristics of physical solvents, any acidic components that are present in the inlet gas to the Mehra process, whether existing in the gas phase subsequent to amines treatment or when there is no removal of acidic components from the gas phase, will end up in the liquid product. The residue natural gas stream will always meet pipeline specifications even if no gas phase treatment of acid components is employed because the physical solvent will ensure desired sweetness thereof. However, the concentration effect, due to the absence of methane in the natural gas liquids product, may make such a product unacceptable due to the specifications for acidic components. Thus a final treatment would be necessary for most situations to ensure that the NGL product meets all required specifications.

If substantial quantities of $H_2S$ are present along with $CO_2$ in an inlet natural gas, it may be required, because of environmental law, to convert $H_2S$ to sulfur in a Claus plant. A treating system may have to be designed such that the regenerated solution rejects the acid gas consistently with the requirements of the Claus plant for sulfur recovery. Therefore, such a prior treatment would leave remaining quantities of $CO_2$ in the inlet natural gas stream to the Mehra process. Such $CO_2$ quantities will end up in the NGL product, thereby making it unacceptable for sale and requiring a liquid-stage treatment of this NGL product.

DESCRIPTION OF THE PREFERRED EMBODIMENT

Figure 5:
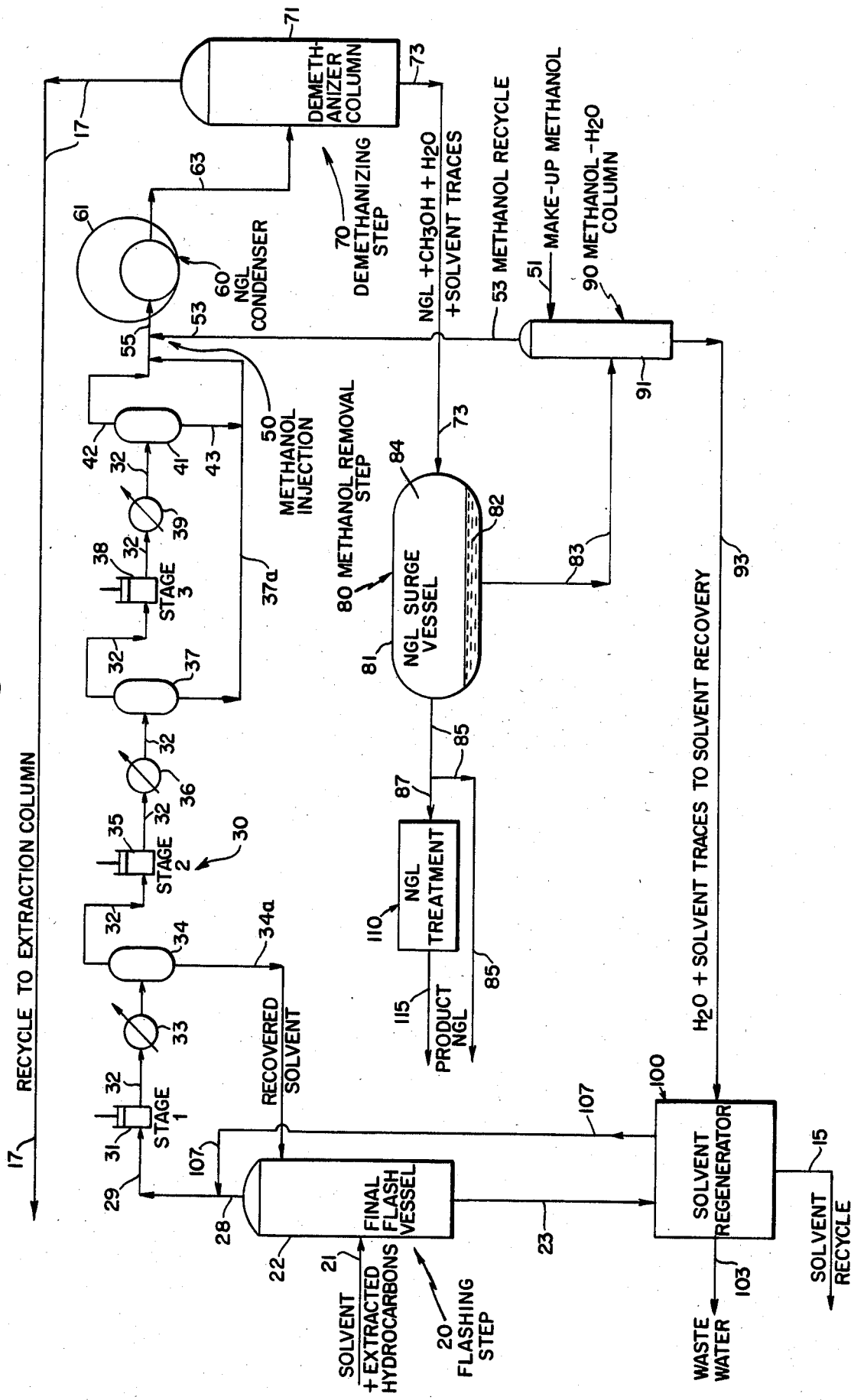
FIG. 5 is a schematic process flowsheet which enlarges the freeze protection system and NGL product treatment of FIG. 4.

Referring to FIGS. 4 and 5, sweet natural gas which is saturated with water enters extraction unit 10, which includes an extraction column, through feed line 11. Selectively rejected $C_1$–$C_4$ gases also enter extraction Step 10 through line 17 and $C_1$-rich flashed gases additionally enter extraction unit 10 through line 25. A physical solvent is fed to extraction unit 10 through line 15. Countercurrent passage of solvent and natural gas results in residue natural gas leaving the top of the column through line 13 as sales gas and rich solvent leaving the bottom of the column through line 19.

More specifically, the rich solvent in line 19 is fed to the first stage of at least two flashing stages in flashing unit 20. The $C_1$-rich flashed gases from all stages operating at pressures above atmospheric pass through line 25 to the bottom of the extraction column. A stream 21 of solvent and extracted hydrocarbons enter final flash vessel 22. The stream of $C_1$-lean flashed gases from the final flash vessel 22, which may be the atmospheric flashing stage or the vacuum flashing stage, passes through line 28 and receives a minor hydrocarbon stream in line 107 from solvent regenerating unit 100. The combined streams in line 29 enter first-stage compressor 31 of compression and cooling unit 30. Moving through line 32, the stream passes through cooler 33 to enter separator 34, wherein solvent separates from the hydrocarbon vapors and then returns to the final flashing stage through line 34a. Continuing now through line 32, the vapors are further compressed by second-stage compressor 35, are cooled by cooler 36, and enter separator 37, from the top of which hydrocarbons containing traces of solvent move to third stage compressor 38, cooler 39, and separator 41. Vapors from the top of separator 41 leave through line 42. Meanwhile, liquid hydrocarbons in the bottom of separator 37 leave through line 37a, receive additional liquid through line 43 from the bottom of separator 41, and join line 42.

At this point, the combined stream in line 42, representing $C_1$-lean hydrocarbons, enters methanol injection unit 50 wherein it receives methanol from line 53. The mixture of $C_1$-lean flashed gases and methanol solution passes through line 55 to enter condensing unit 60. In condensing unit 60, the temperature ranges from $+60°$ F. to $-30°$ F. The stream 63 leaving condenser 61 enters column 71 of demethanizing unit 70.

The vapors from the top of column 71, comprising selectively rejected $C_1$-$C_4$ components of the raw natural gas, leave through line 17 to be fed to the bottom of the extraction column. The liquid in the bottom of column 71, as a methanol/water/solvent/hydrocarbon mixture, passes through line 73 to methanol removal unit 80, comprising NGL surge vessel 81. Using well known procedures, the methanol/water/solvent phase within bottom layer 82 is decanted and passed through line 83 to methanol clean-up system 90. Within column 91 of methanol cleanup system unit 90, the methanol/water/solvent solution is separated into a substantially pure stream of methanol, which leaves through line 53 for juncture with line 42, and a stream of water and solvent, which passes through line 93 to solvent regeneration unit 100. Upper phase 84, occupying substantially all of vessel 81, is removed through line 85 as the natural gas liquid products which meet product specifications with respect to water and are free of traces of residual solvent. The NGL products are removed through line 85. Make-up methanol is added through line 51.

When the NGL products contain an excessive amount of acid components, they are diverted through line 87 to NGL treatment unit 110. Treated product leaves through line 115. The solvent regeneration unit 100 receives a solvent/water/ hydrocarbons mixture through line 23 and a solvent/water mixture through line 93. In unit 100, a vaporized mixture of trace hydrocarbons and water is condensed and separated into waste water, which is discharged through line 103, and hydrocarbon vapors, which are returned to line 28 through line 107. Regenerated solvent, which is lean with respect to hydrocarbons and dry with respect to water, is recycled to the top of the extraction column of extraction Step 10 through line 15.

Flashing the enriched solvent stream, the rich solvent stream, or a mixture of these solvent streams to approximately atmospheric pressure in at least two stages provides optimum efficiency for this improved Mehra process. Nevertheless, there are some small plants which have insufficient throughput, such as approximately one million cubic feet of raw natural gas per day, to justify a compressor for the $C_1$-rich flashed gases. For such small plants, it is economically preferable to use a single flashing stage which produces a single flashed gas stream of $C_2+$ hydrocarbons (plus possibly substantial amounts of methane) for feeding to the demethanizer. This modification of the Mehra process imposes a heavier load on the demethanizer and higher operating costs for demethanizing, but it saves on capital expenditures.

The pressure drop in the single flashing stage should reduce the pressure from wellhead or line pressure of up to 1300 psia to a pressure as low as 2 psia, but the exemplary terminal pressure after flashing may be 100 psia, 50 psia, atmospheric pressure, or, rarely, a vacuum, depending upon plant conditions which may include piggy-back utilization of existing plant equipment. In contrast, plants having a very large throughput may utilize as many as eight flashing stages, having ratios of absolute pressures of successive flashing stages of at least 2.0, in order to minimize energy consumption.

Any pressure drop and any number of flashing stages can be utilized for the Mehra process in general and for this improvement thereof, but it is preferred that at least two flashing stages be used in order to increase flashing efficiency and especially to be able to isolate and recycle to the extractor the stream of $C_1$-rich flashed gases without having to additionally compress and condense these gases and then pass them through the demethanizer.

If the inlet natural gas stream should be dry, there would be no need for preventing hydrate formation in $C_1$-lean flashed gases. However, there would still be a need for removing trace quantities of solvent from the natural gas liquid product so that it could meet specifications relating to its content of gumming compounds. The process of this invention is able to provide such removal by continuing to utilize methanol injection. However, the methanol may be injected anywhere within the cooling and condensing steps (see FIGS. 3 and 4), as long as it is injected prior to the demethanizing step.

What is regarded as the invention and is desired to be protected is defined in the accompanying claims.

What is claimed is:

1. In a continuous process for producing a liquid hydrocarbon product having a selected composition, that is selectively adjustable to substantially any selected degree in accordance with market conditions, and a residue natural gas stream of pipeline quality, that selectively includes ethane ($C_2$), propane ($C_3$), and butane ($C_4$), by extraction of an inlet natural gas stream with a stream of a physical solvent to produce a rich solvent stream in addition to said residue natural gas stream, said rich solvent stream being flashed to at least atmospheric pressure to produce:

(a) stream of flashed gases which are compressed, cooled, and condensed for demethanizing to produce a selected stream of $C_1$-$C_4$ rejected gases and a natural gas liquid product, and (b) a recycle solvent stream that is split into a major solvent stream and a solvent slipstream which is regenerated to form a lean-and-dry solvent stream for recycling to said extraction, wherein needs exist for:
  (i) removing resiudal water from flashed gases before the hydrate temperature is reached after compressing and cooling thereof,
  (ii) removing residual solvent from said natural gas liquid product, so that said solvent will not act as a gumming compound when a natural gasoline fraction of said natural gas liquid product is used for motor fuel, and
  (iii) sweetening said natural gas liquid product when sour natural gas has been given merely a rough wash selectively to remove $H_2S$ to prepare said natural gas for said continuous process, an improvement which comprises preventing the formation of hydrates within said flashed gases and removing water, residual solvent, and traces of acidic components from said natural gas liquid product by the following steps:
  A. adding methanol to said stream of flashed gases, prior to achieving the temperature for hydrate formation;
  B. after said demethanizing, separating the mixture of a methanol/water/solvent solution and a natural gas liquid product into two phases, the lower phase being said solution of methanol, water and solvent;
  C. removing said lower phase and fractionating said solution to recover said methanol overhead and a stream of water and solvent; and
  D. recycling said recovered methanol to said stream of flashed gases in said step A.

2. The improved process of claim 1, wherein said compressed, cooled, and condensed stream of flashed gases and methanol is at a temperature of $+60°$ F. to $-30°$ F.

3. The improved process of claim 2, wherein said compressed, cooled, and condensed stream of flashed gases and methanol is at a temperature of $+30°$ F. to $-20°$ F.

4. The improved process of claim 3, wherein said stream of flashed gases and methanol is at a maximum pressure of 500 PSIA after said compressing, cooling, and condensing.

5. In a process that provides the capability of selectively extracting natural gas liquids from an inlet natural gas stream containing water up to saturation with a physical solvent according to any selected degree and at extremely high recoveries of the following components of said natural gas stream:
  (a) ethane in amounts ranging from 2–98%,
  (b) propane in amounts ranging from 2–99%,
  (c) butane in amounts ranging from 2–100%; or
  (d) pentanes and higher molecular weight hydrocarbons in amounts ranging up to 100%, said process comprising the following steps:
  (a) extracting said inlet natural gas stream with said physical solvent at flow rates within the range of 0.005–0.5 gallon of solvent per standard cubic foot of natural gas to produce a residue natural gas stream of pipeline specifications and a rich solvent stream containing said extracted ethane and heavier hydrocarbon components, said solvent being selective for said ethane and heavier hydrocarbon components of said natural gas stream such that the relative volatility of methane over ethane is at least 5.0 and the hydrocarbon loading capacity, defined as solubility of ethane in solvent, is at least 0.25 standard cubic feet of ethane per gallon of solvent;
  (b) selectively flashing said rich solvent stream to produce:
    (1) a stream of $C_1$-rich flashed gases which is recycled for extraction with said physical solvent stream,
    (2) a stream of $C_1$-lean flashed gases, and
    (3) a recycle solvent stream that is split into a major solvent stream and a solvent slipstream which is regenerated to form a lean-and-dry solvent stream for recycling to said extraction step,
  (c) compressing, cooling, and condensing said stream of $C_1$-leans flashed gases, and
  (d) demethanizing said condensed $C_1$-lean flashed gases to form a natural gas liquid product, wherein there is a need for removal of residual solvent and residual water from said natural gas liquid product, so that said solvent will not act as a gumming compound when a natural gasoline fraction of said natural gas liquid product is used for motor fuel, the improvement which comprises removing said residual solvent and said residual water and preventing the formation of hydrates within said $C_1$-lean flashed gases to form a purified natural gas liquid product by the following steps:
  A. adding methanol to said stream of $C_1$-lean flashed gases, prior to achieving the temperature for hydrate formation, to form a mixture for said demethanizing step;
  B. after said demethanizing, separating the demethanized mixture into two phases, the lower phase being a solution of methanol, water, and solvent and the upper phase being said purified natural gas liquid product;
  C. removing said lower phase and fractionating said solution to recover said methanol overhead and a stream of water and solvent as bottoms;
  D. recycling said recovered methanol to said stream of $C_1$-lean flashed gases in said Step A; and
  E. removing said upper phase and recovering said purified natural gas liquid product.

6. The improved process of claim 5, wherein said compressed, cooled, and condensed stream of $C_1$-lean flashed gases and methanol is at a temperature of $+60°$ F. to $-30°$ F.

7. The improved process of claim 6, wherein said compressed, cooled, and condensed stream of $C_1$-lean flashed gases and methanol is at a temperature of $+30°$ F. to $-20°$ F.

8. The improved process of claim 6, wherein said stream of $C_1$-lean flashed gases and methanol is at a maximum pressure of 500 PSIA after said compressing, cooling, and condensing.

9. The improved process of claims 8 or 4, wherein said purified natural gas liquid product is recovered as the upper phase of said two phases.

10. The improved process of claim 9, wherein said inlet natural gas stream is selected from the group consisting of:
  A. natural gas saturated with water;
  B. natural gas at less than saturation with water;
  C. sour natural gas;

D. sour natural gas which is pre-sweetened in gas phase with an aqueous amine solution;

E. sweet natural gas; and

F. dry natural gas.

11. The improved process of claim 10, wherein said residue natural gas contains less than 7 pounds of water vapor per million standard cubic feet as said selected degree.

12. The improved process of claim 11, wherein said physical solvent is selective toward ethane and heavier hydrocarbon components of said inlet natural gas stream over methane, such that the relative volatility of methane over ethane is at least 5.0 and the hydrocarbon loading capacity, defined as solubility of ethane in solvent, is at least 0.25 standard cubic feet of ethane per gallon of solvent.

13. The improved process of claim 12, wherein said physical solvent is selected from the group consisting of dialkyl ethers of polyalkylene glycol, N-methyl pyrrolidone, dimethyl formamide, propylene carbonate, sulfolane, and glycol triacetate.

14. The improved process of claim 13, wherein said solvent is selected from the group consisting of dimethyl ether of polyethylene glycol, dimethyl ether of polypropylene glycol, dimethyl ether of tetramethylene glycol, and mixtures thereof.

15. The improved process of claim 14, wherein said solvent is dimethyl ether of polyethylene glycol containing 3–10 ethylene units and having a molecular weight of 146 to 476.

16. The improved process of claim 10, wherein said inlet natural gas stream is said sour natural gas which has acidic components and said purified natural gas liquid product also contains said acidic components.

17. The improved process of claim 16, wherein said purified natural gas liquid product is further treated with a chemically reactive stream to remove said acidic components therefrom.

18. The improved process of claim 17, wherein said chemically reactive stream comprises an aqueous amine solution.

19. In a process that provides the capability of selectively extracting natural gas liquids from an inlet natural gas stream, selected from the group consisting of dry and sweet natural gas, dry and sour natural gas, wet and sweet natural gas, and wet and sour natural gas, with a physical solvent according to any selected degree and at extremely high recoveries of the following components of said natural gas stream:

(a) ethane in amounts ranging from 2–98%, (b) propane in amounts ranging from 2–99%, (c) butane in amounts ranging from 2–100%; or (d) pentanes and higher molecular weight hydrocarbons in amounts ranging up to 100%, said process comprising the following steps:

(a) extracting said inlet natural gas stream with said physical solvent at flow rates within the range of 0.005–0.5 gallon of solvent per standard cubic foot of natural gas to produce a residue natural gas stream of pipeline specifications and a rich solvent stream containing said extracted ethane and heavier hydrocarbon components, said solvent being selective for said ethane and heavier hydrocarbon components of said natural gas stream such that the relative volatility of methane over ethane is at least 5.0 and the hydrocarbone loading capacity, defined as solubility of ethane in solvent, is at least 0.25 standard cubic feet of ethane per gallon of solvent;

(b) selectively flashing said rich solvent stream to produce:

(1) a stream of $C_1$-rich flashed gases which is recycled for extraction with said physical solvent stream, (2) a stream of $C_1$-lean flashed gases, and (3) a recycle solvent stream that is split into a major solvent stream and a solvent slipstream which is regenerated to form a lean-and-dry solvent stream for recycling to said extraction step, (c) compressing, cooling, and condensing said stream of $C_1$-lean flashed gases, and (d) demethanizing said condensed $C_1$-leans flashed gases to form a natural gas liquid product, wherein said inlet natural gas stream is dry and sweet and there is a need for removal of residual solvent from said natural gas liquid product, so that said solvent will not act as a gumming compound when a natural gasoline fraction of said natural gas liquid product is used for motor fuel, the improvement which comprises removing said residual solvent to form a purified natural gas liquid product by the following steps:

A. adding methanol to said stream of $C_1$-lean flashed gases to form a mixture for said demethanizing step (d);

B. after said demethanizing, separating the demethanized mixture into two phases, the lower phase being a solution of methanol and solvent and the upper phase being said purified natural gas liquid product.

20. The improved process of claim 19, wherein said inlet natural gas stream is wet and sweet and wherein there is a need for removal of residual water and said residual solvent from said $C_1$-lean flashed gases before or during cooling thereof, whereby the improvement comprises removing residual solvent and residual water and preventing the formation of hydrates within said $C_1$-lean flashed gases to form a purified natural gas liquid product, said improved process comprising the following steps:

A. adding methanol to said stream of $C_1$-lean flashed gases, prior to achieving the temperature for hydrate formation, to form a mixture for said demethanizing step (d); and B. after said demethanizing, separating the demethanized mixture into two phases, the lower phase being a solution of methanol, water, and solvent and the upper phase being said purified natural gas liquid product.

21. The improved process of claim 19, wherein said inlet natural gas stream is wet and sweet after a rough amine wash and contains small amounts of acid gases and wherein there is a need for removal of residual water, residual solvent, and at least traces of acid gases from said $C_1$-lean flashed gases before or during cooling thereof, the improvement which comprises removing residual solvent, residual water, and said traces of acid gases and preventing the formation of hydrates within said $C_1$-lean flashed gases to form a purified natural gas liquid product, said improved process comprising the following steps:

A. adding methanol to said stream of $C_1$-lean flashed gases, prior to acheiving the temperature for hydrate formation, to form a mixture for said demethanizing step (d); and
B. after said demethanizing, separating the demethanized mixture into two phases, the lower phase being a solution of methanol, water, solvent, and acid gases and the upper phase being said purified natural gas liquid product.

* * * * *